(12) United States Patent
Williams et al.

(10) Patent No.: US 12,588,134 B2
(45) Date of Patent: Mar. 24, 2026

(54) AIR DIRECTING SCOOP FOR HEAT SINK AND UV-C APPARATUS

(71) Applicant: C & W Specialty Holdings LLC, Horseheads, NY (US)

(72) Inventors: Colin Williams, Endicott, NY (US); Daniel Coon, Owego, NY (US); Gregory Cleveland, Owego, NY (US); Stephen Marcy, Hallstead, PA (US)

(73) Assignee: UV-CLEAR, INC, Horseheads, NY (US)

( * ) Notice: Subject to any disclaimer, the term of this patent is extended or adjusted under 35 U.S.C. 154(b) by 354 days.

(21) Appl. No.: 18/328,315

(22) Filed: Jun. 2, 2023

(65) Prior Publication Data

US 2023/0397322 A1     Dec. 7, 2023

Related U.S. Application Data

(60) Provisional application No. 63/365,750, filed on Jun. 2, 2022.

(51) Int. Cl.
*F24F 8/22* (2021.01)
*A61L 9/20* (2006.01)
(Continued)

(52) U.S. Cl.
CPC .............. *H05K 1/0203* (2013.01); *A61L 9/20* (2013.01); *F24F 8/22* (2021.01); *F24F 13/08* (2013.01);
(Continued)

(58) Field of Classification Search
CPC ............... H05K 1/0203; H05K 7/2039; H05K 2201/10106; H05K 2201/066; F24F 8/22;
(Continued)

(56) References Cited

U.S. PATENT DOCUMENTS

| | | | |
|---|---|---|---|
| 8,252,100 B2 | 8/2012 | Worrilow | |
| 9,980,748 B2 | 5/2018 | Worrilow | |

(Continued)

FOREIGN PATENT DOCUMENTS

| | | |
|---|---|---|
| CN | 108151177 | 6/2018 |
| CN | 108844137 | 11/2018 |

(Continued)

OTHER PUBLICATIONS

International Search Report and Written Opinion (ISA: USPTO); Mar. 4, 2024; International App. No. PCT/US2023/082076.

*Primary Examiner* — Uzma Alam
(74) *Attorney, Agent, or Firm* — Simpson & Simpson, PLLC; Kevin Michael Bronson; Robert P. Simpson

(57) ABSTRACT

An air sanitizing apparatus arranged within an HVAC duct having an air scoop, the air scoop arranged on a surface of the HVAC duct, the air scoop having an inlet end and an outlet end, the air scoop having a bracket extending distally from the air scoop, a UV light module, the UV light module secured to the bracket, the UV light module having a temperature sensor, a heat sink, the heat sink secured to the UV light module and proximate to the outlet end and, a control board, the control board in communication with the UV light module, the control board having a microprocessor in communication with an ambient temperature sensor and a heat-source temperature sensor arranged proximate to an external heat source, the microprocessor in communication with the temperature sensor of the UV light module.

20 Claims, 11 Drawing Sheets

(51) Int. Cl.

| | |
|---|---|
| *F24F 13/08* | (2006.01) |
| *F24F 13/30* | (2006.01) |
| *G01K 7/22* | (2006.01) |
| *H05K 1/02* | (2006.01) |
| *H05K 7/20* | (2006.01) |

(52) U.S. Cl.
CPC ............... *F24F 13/30* (2013.01); *G01K 7/22* (2013.01); *H05K 7/2039* (2013.01); *A61L 2209/12* (2013.01); *A61L 2209/16* (2013.01); *H05K 2201/10106* (2013.01)

(58) Field of Classification Search
CPC ........ F24F 13/08; F24F 13/30; F24F 2110/10; A61L 9/20; A61L 2209/12; A61L 2209/16; A61L 2209/111; G01K 7/22
See application file for complete search history.

(56) References Cited

U.S. PATENT DOCUMENTS

| | | | |
|---|---|---|---|
| 11,160,897 | B1 | 11/2021 | Shalvi |
| 11,357,882 | B2 | 6/2022 | Dunbar |
| 12,102,723 | B2 * | 10/2024 | James .......................... A61L 2/10 |
| 2008/0019861 | A1 | 1/2008 | Silderhuis |
| 2014/0294666 | A1 * | 10/2014 | Liu ............................ A61L 9/00 422/4 |
| 2019/0009912 | A1 * | 1/2019 | Matsui ..................... B64D 13/02 |
| 2020/0108166 | A1 | 4/2020 | Rhoden |
| 2022/0023482 | A1 | 1/2022 | Skelton |
| 2022/0047767 | A1 | 2/2022 | McConnaughey et al. |
| 2022/0152265 | A1 | 5/2022 | Eggers |
| 2022/0193280 | A1 * | 6/2022 | James .......................... A61L 9/20 |
| 2022/0234002 | A1 * | 7/2022 | Trent ..................... B01D 53/75 |
| 2022/0305881 | A1 * | 9/2022 | Neu ..................... B60H 1/00364 |

FOREIGN PATENT DOCUMENTS

| | | | | |
|---|---|---|---|---|
| CN | 208901577 | | 5/2019 | |
| CN | 111102659 | | 5/2020 | |
| FR | 3063538 | | 9/2018 | |
| JP | 2024151773 A | * | 10/2024 | |
| WO | WO-2022086965 A1 | * | 4/2020 | ............... A61L 9/20 |
| WO | WO-2024102899 A2 | * | 5/2024 | ............... A61L 9/20 |

* cited by examiner

AIR DIRECTING SCOOP FOR HEAT SINK AND UV-C APPARATUS

CROSS-REFERENCE TO RELATED APPLICATIONS

This application claims priority pursuant to 35 U.S.C. § 119 to U.S. Provisional Application No. 63/365,750, filed on Jun. 2, 2022, the entire contents of which are incorporated by reference in its entirety herein.

FIELD

The present invention generally relates to an apparatus arranged to secure a UV-C (ultraviolet) light module within an HVAC (heating ventilation air conditioning) duct where the apparatus is arranged to direct air flow within the duct over a heat sink apparatus arranged on the UV light module.

BACKGROUND

Indoor air filtration is well known within the art. In expensive filtration apparatuses, mechanical filtration is commonly utilized, such as the use of filters. It is well known that UV-wavelength light also provides radiation filtration of air.

Unlike other air filtration systems that depend on HEPA (high efficiency particulate air) filters or other like devices to trap dust and other particles, UV air filtration uses state-of-the-art ultraviolet light technology to keep viruses and other microorganisms from reproducing and infecting a home, office, or other indoor space. Ultraviolet light damages the genetic material that controls the reproduction of these organisms, making it impossible for them to reproduce. UV light stops these illness-inducing microbes and prevents the spread of various diseases and other problems.

UV purification is most effective when the microorganisms have prolonged contact with the UV lamp. The longer that a virus or other organism is bathed in UV light, the greater the damage to its DNA and its ability to replicate itself. There are three types of UV light: UV-A, UV-B, and UV-C-differentiated by the wavelength of the light. UV-A light has the largest wavelength, ranging from 315-400 nm. UV-C light has the shortest wavelength, from 100-280 nm. As UV-C light has the shortest wavelength, it also has the most energy of the UV light types. Meaning UV-C light has the most power to destroy genetic material within viruses and other microbes. UV-C light at a specific wavelength of approximately 254 nm has been found to be effective in killing coronavirus such as a severe acute respiratory virus (SARS-COV) and Middle Eastern Respiratory Syndrome (MERS-COV) as well as other viruses such as H1N1 influenza—approximately 267 nm is the preferable wavelength for best results. UV lights used for disinfection generate UV-C with wavelengths in the approximate range of 250-280 nm. Approximately 250-280 nm UV light is commonly acknowledged as the germicidal UV-C range.

In previous attempts to utilize UV treatment, an apparatus was used to treat air within a duct with a negative oxygen enhancer. The apparatus includes a baffle which is arranged to direct the incoming air flow in a direction proximate the negative oxygen enhancer. A temperature sensor within the apparatus is arranged to measure the temperature of the incoming air and, when the measured temperature is less than a predetermined temperature, the negative oxygen enhancer is programmed to turn off. The negative oxygen enhancer also includes a UV light apparatus which irradiates water released from a water tank and into the air passing through the air duct to treat the air before exiting the apparatus.

In another attempt to use UV treatment, an air filtration/purification device generally includes a housing, where the housing is defined by an inlet end and an outlet end. A fan, arranged to move air through the device, is positioned proximate the inlet end. Disposed proximate the outlet end are a VOC (volatile organic compounds) filtration device, a final particulate filtration means and a humidifier. Within the device, at least one UV lamp is disposed therein, aiding in the filtration of air passing through.

UV wavelengths, specifically LED-emitted UV-C wavelengths, generate a considerable amount of heat from their respective light source or sources. Extended heat exposure degrades the light sources, e.g., LED light sources, such that excess heat alters the wavelengths of the light emitted therefrom and decreases the longevity of the light-emitting devices.

Thus, there is a long-felt need for an apparatus that utilizes UV-C to treat air flowing through an HVAC apparatus, where the apparatus is further arranged to direct the airflow onto a heat dissipation apparatus arranged on a UV-C light module, that is further arranged to measure the incoming airflow and selectively toggle the UV-C light module on and off based on measured variables, to manage heat of the UV-C apparatus.

Additionally, there is also a long-felt need for a UV-C light module including a plurality of individual heat sinks arranged to manage heat dissipation of individual UV LED lights.

Further, there is another long-felt need for a UV light air-treatment apparatus that can be installed into an existing HVAC structure with minimal components and minimal disruption of the existing structure.

SUMMARY

The present invention generally is arranged to be installed into commercial and residential air duct systems to purify the air moving through the air duct systems. The present invention aims to be a replacement, economical alternative, or supplemental, for typical air filtration systems within established HVAC structures, or other air-movement systems, by providing cleaner air via UV radiation with less required maintenance.

The present invention broadly comprises an air sanitizing apparatus arranged within an HVAC duct having an air scoop, the air scoop arranged on a surface of the HVAC duct, the air scoop having an inlet end and an outlet end, the air scoop having a bracket extending distally from the air scoop, a UV light module, the UV light module secured to the bracket, the UV light module having a temperature sensor, a heat sink, the heat sink secured to the UV light module and proximate the outlet end and, a control board, the control board in communication with the UV light module, the control board having a microprocessor in communication with an ambient temperature sensor and a heat-source temperature sensor arranged on an external heat source, the microprocessor in communication with the temperature sensor of the UV light module.

The present invention also broadly includes a PCB board to which the UV light module is secured, the UV light module including a plurality of LED light modules, each of the plurality of LED light modules arranged to emit UV-C.

The heat sink of the present invention further comprises a plurality of radiator fins arranged to extend beyond the UV light module, the plurality of radiator fins having an upper portion and a lower portion, wherein the upper portion and the lower portion of the plurality of radiator fins are secured to the bracket and are further arranged perpendicularly to a pair of mounting faces of the bracket, wherein the upper portion of the plurality of radiator fins is disposed within the air scoop and the lower portion of the plurality of radiator fins extend past the outlet end of the air scoop.

The UV light module of the present invention further comprises a plurality of individual heat sinks secured to the PCB board, each of the plurality of individual heat sinks disposed adjacent to each of the plurality of LED light modules, where each of the plurality of individual heat sinks includes a plurality of fins.

As stated supra, a primary object of the present invention is to provide for an air sanitation apparatus utilizing UV radiation.

Another object of the present invention is to provide for an air sanitation apparatus that comprises minimal installation components within an existing HVAC system.

A further object of the present invention is to utilize a temperature comparison protocol to initiate a power on or a power off function of the UV light module, where the protocol improves the longevity of the individual LEDs of the UV light module and provides for efficient energy consumption of the apparatus, specifically the UV light module in response to air flow within the HVAC duct, or air passageway.

A still further object of the present invention is to provide for a heat mitigation apparatus that directs air flowing through an HVAC system into a heat sink apparatus.

An even further object of the present invention is to provide for individual heat mitigation apparatuses disposed adjacent to the individual LEDs of the UV light module.

Another further object of the present invention is to provide for an air sanitation apparatus having a fault-detection protocol that is communicated to an onboard microcontroller, i.e., a control module, that can be stored in the module, or, alternatively, communicated to an external device.

These and other objects, features, and advantages of the present invention will become readily apparent upon a review of the following detailed description of the invention, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Figures 1A, 1B:
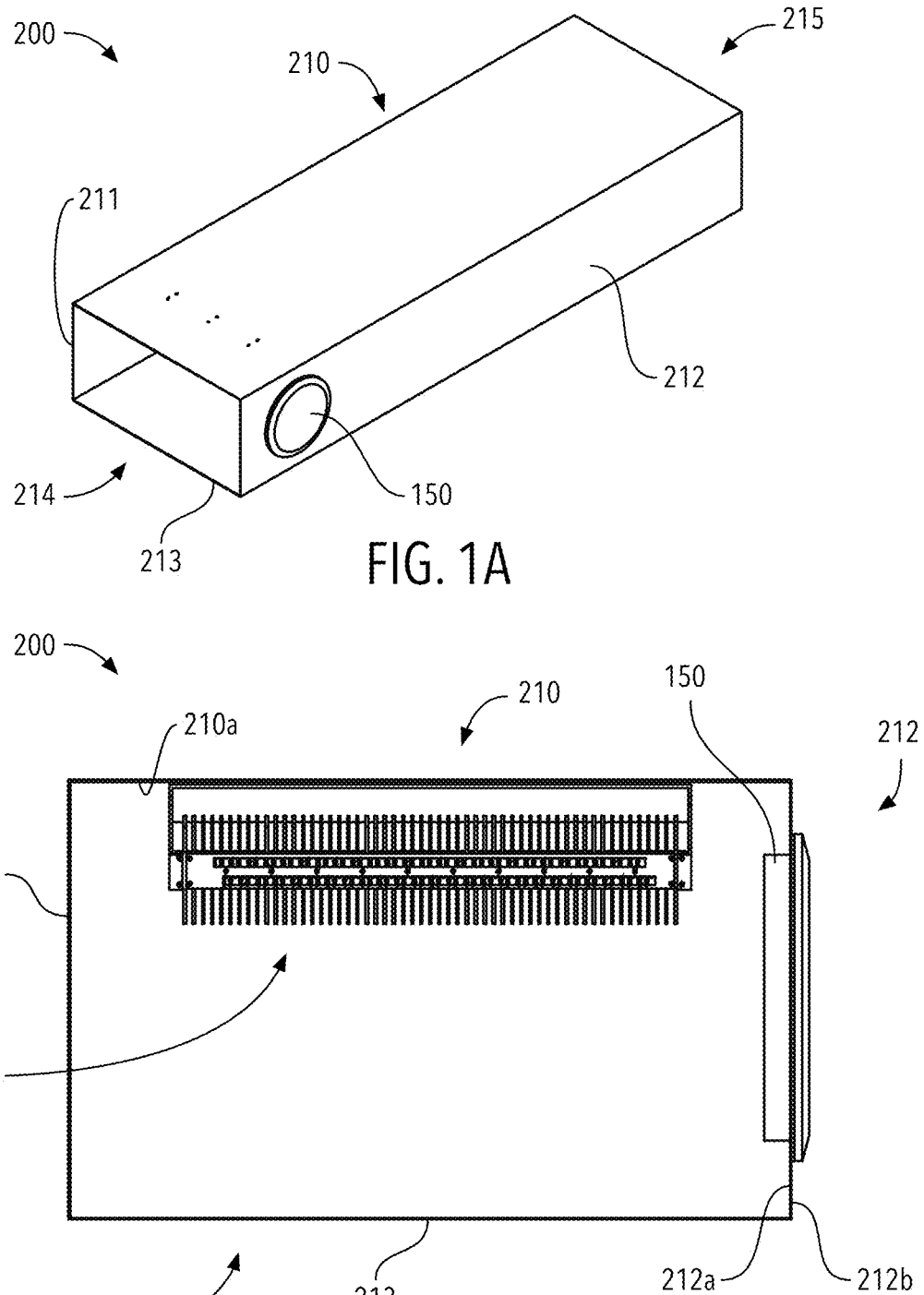
FIG. 1A is a perspective view of an HVAC duct.
FIG. 1B is a front view of the present invention.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only and is not intended to limit the scope of the claims. As such, those in the art will understand that in any suitable material, now known or hereafter developed, may be used in forming the present invention and/or components of the present invention, as described herein.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" or "one of:", is used herein.

It should be appreciated that the embodiments as illustrated are only one of a variety of possible embodiments of the claimed invention. It should also be appreciated that directional adjectives, such as "upper", "lower", "right", "left", and similar variations, are to be interpreted in view of the corresponding drawings and are intended to be exemplary.

It should be noted that the terms "having", "has", "including", "includes", "containing", and "contains", are intended to be interpreted as substantially synonymous to the terms "comprising" and/or "comprises".

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

Figure 2A:
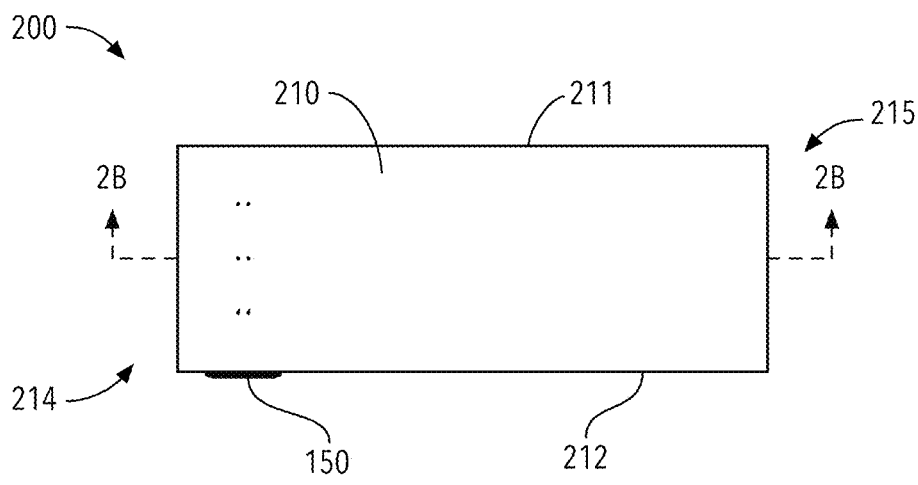
FIG. 2A is a top view of the HVAC duct shown in FIG. 1A.
Figure 2B:
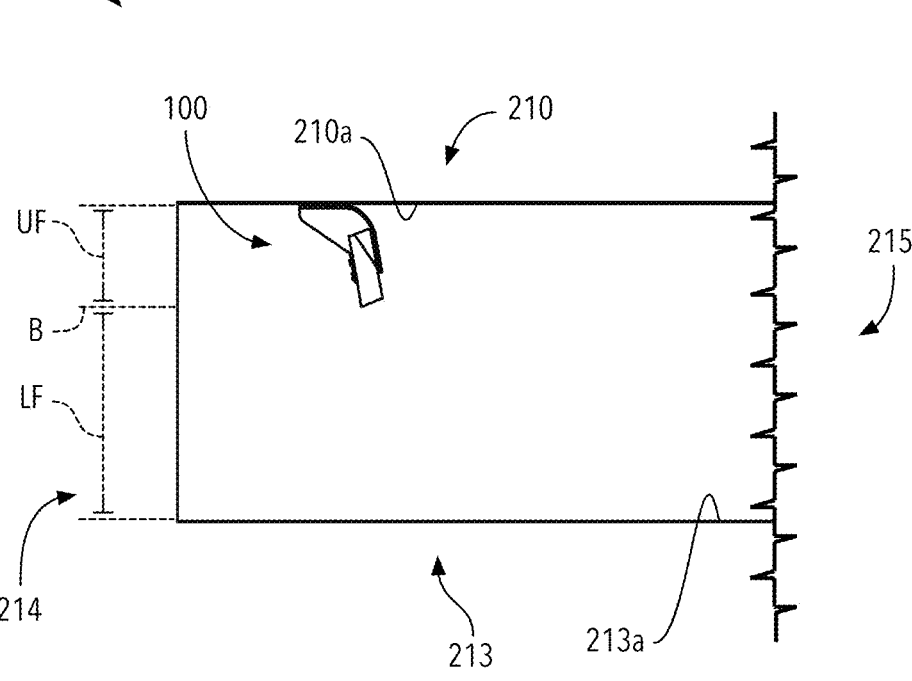
FIG. 2B is a cross-sectional view of the HVAC duct taken generally along line 2B-2B in FIG. 2A, with the present invention installed therein.

Adverting now to the figures. The following description should be taken in view of FIGS. 1A and 2B. FIG. 1A illustrates a perspective view of HVAC duct 200. FIG. 1B illustrates a front view of the heat duct shown in FIG. 1A having UV-C air scoop apparatus 100 attached therein. FIG. 2A illustrates a top view of HVAC duct 200 having UV-C air scoop apparatus 100 attached therein and FIG. 2B is a cross-sectional view of the duct, taken generally along line 2B-2B in FIG. 2A.

Although FIGS. 1A-2B illustrate HVAC duct 200 having a generally rectangular configuration, it should be appreciated that HVAC duct 200 may comprise a circular, tubular configuration, where UV-C air scoop apparatus 100 may be adapted to include a curvature to accommodate the curved configuration of the HVAC duct. It should be noted that the illustrations of HVAC duct 200 are portions of an entire HVAC duct system, and that other shapes of ducts are considered to be within the scope of the appended claims.

HVAC duct 200 is generally formed by top member 210, first side member 211, second side member 212, and bottom member 213. HVAC duct 200 has inlet end 214 and outlet end 215. Inlet end 214 is defined as the end of HVAC duct 200 that air flows into and outlet end 215 is defined as the end of HVAC duct 200 that air flows out of. In other words, inlet end 214 represents the inflow portion of HVAC duct 200, that is, the section of an HVAC duct system that is attached to, or begins, at an air source, e.g., heating, ventilation, and/or air conditioning, whereas outlet end 215 represents the outflow portion of HVAC duct 200, that is, the section of an HVAC duct system that terminates at an outflow vent or exhaust.

In a preferred embodiment, UV-C air scoop apparatus 100 is arranged to be removably secured to internal surface 210a of top member 210 of HVAC duct 200. In a preferred embodiment, UV-C air scoop apparatus 100 is secured to internal surface 210a via a plurality of screws. However, it should be appreciated that other removable securement means known in the art may be used to secure the apparatus to the duct wall/ceiling. Also arranged on HVAC duct 200 is control module 150 (shown in FIG. 1B) of UV-C air scoop apparatus 100. Control module 150 may be removably secured to internal surface 212a of second side member 212 or removably secured to external surface 212b of second side member 212 or may be disposed within second side member 212 via a cut-out through-bore arranged to accept control module 150 therein.

As shown in FIG. 2B, UV-C air scoop apparatus 100 is configured to bifurcate incoming air from inlet end 214 between internal surface 210a and internal surface 213a, such that its configuration separates the incoming air flow into upper flow UF and lower flow LF at a plane defined by B, and further, where a portion of upper flow UF is arranged to enter UV-C air scoop apparatus 100 to be directed over the heat sink of UV-C air scoop apparatus 100, discussed further infra.

Figures 3A, 3B:
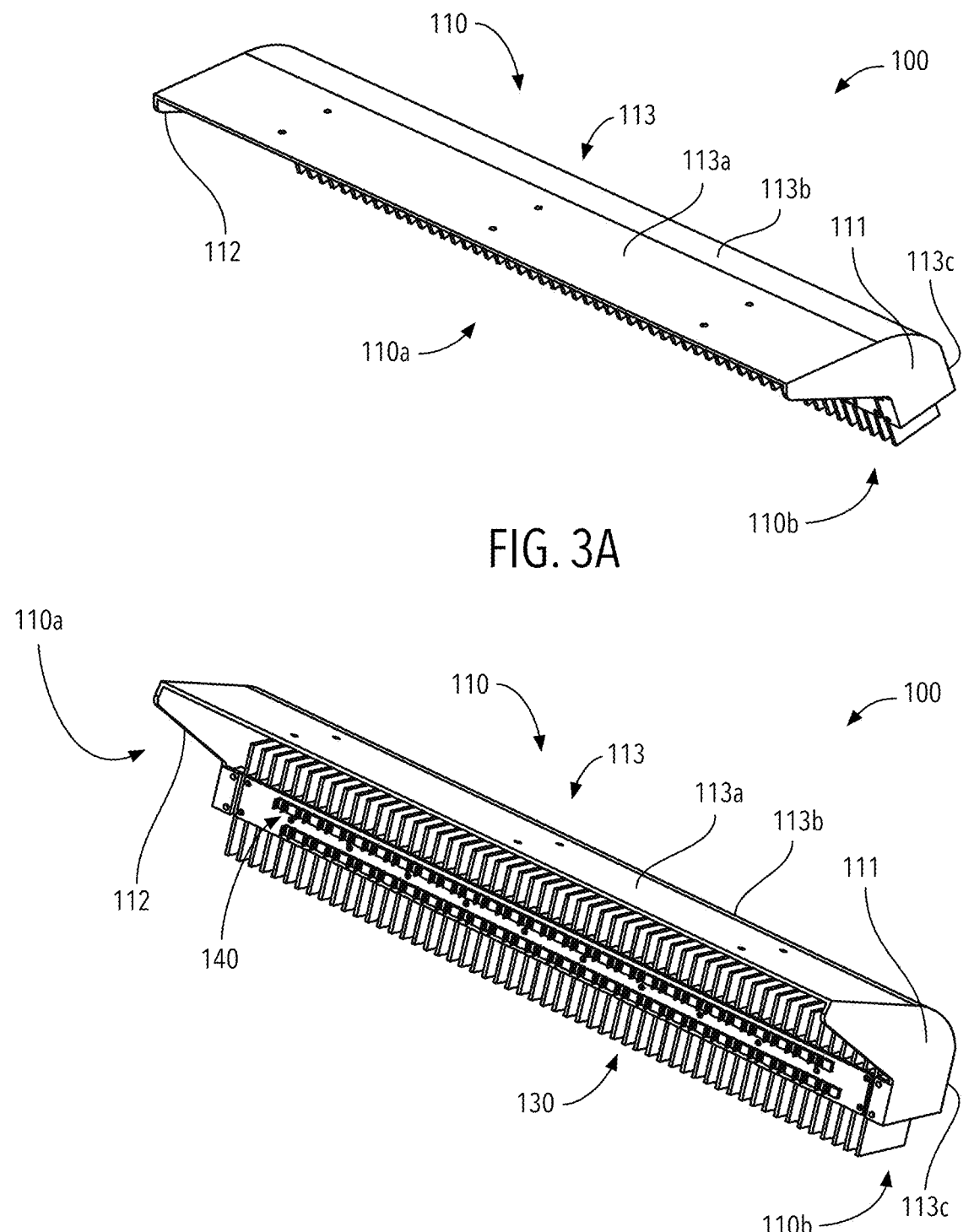
FIG. 3A is a top perspective view of UV-C air scoop apparatus 100 of the present invention.
FIG. 3B is a bottom perspective view of UV-C air scoop apparatus 100 of the present invention.

The following description should be taken in view of FIGS. 3A and 3B. FIG. 3A is a top perspective view of UV-C air scoop apparatus 100, shown removed from HVAC duct 200 and FIG. 3B is a bottom perspective view of the same. UV-C air scoop apparatus 100 generally comprises air scoop 110, heat sink 130, and UV light module 140. Air scoop 110 includes first side panel 111 and second side panel 112. Air directing portion 113 of air scoop 110 is defined by three sections: mounting portion 113a; contoured portion 113b; and, outlet portion 113c. Air scoop 110 has two ends which respectively designate the preferred directional arrangement of UV-C air scoop apparatus 100 when positioned in HVAC duct 200, inlet end 110a and outlet end 110b. Inlet end 110a is the end of UV-C air scoop apparatus 100 that is arranged to accept, or receive, incoming air and outlet end 110b is the end of UV-C air scoop apparatus 100 that the incoming air leaves UV-C air scoop apparatus 100.

Air scoop 110 may be comprised of heat-resistant plastics, polymers, or molded plastics. Air scoop 110 could alternatively be comprised of different lightweight metals. In a preferred embodiment, heat sink 130 may be comprised of aluminum. Heat sink 130 may be alternatively comprised of a copper-nickel combination, stainless steel (e.g., 316, 304, or other suitable stainless steel types), copper, Heresite P413-coated aluminum, E-coated aluminum, or other suitable steel alloys.

Figures 4A, 4B:
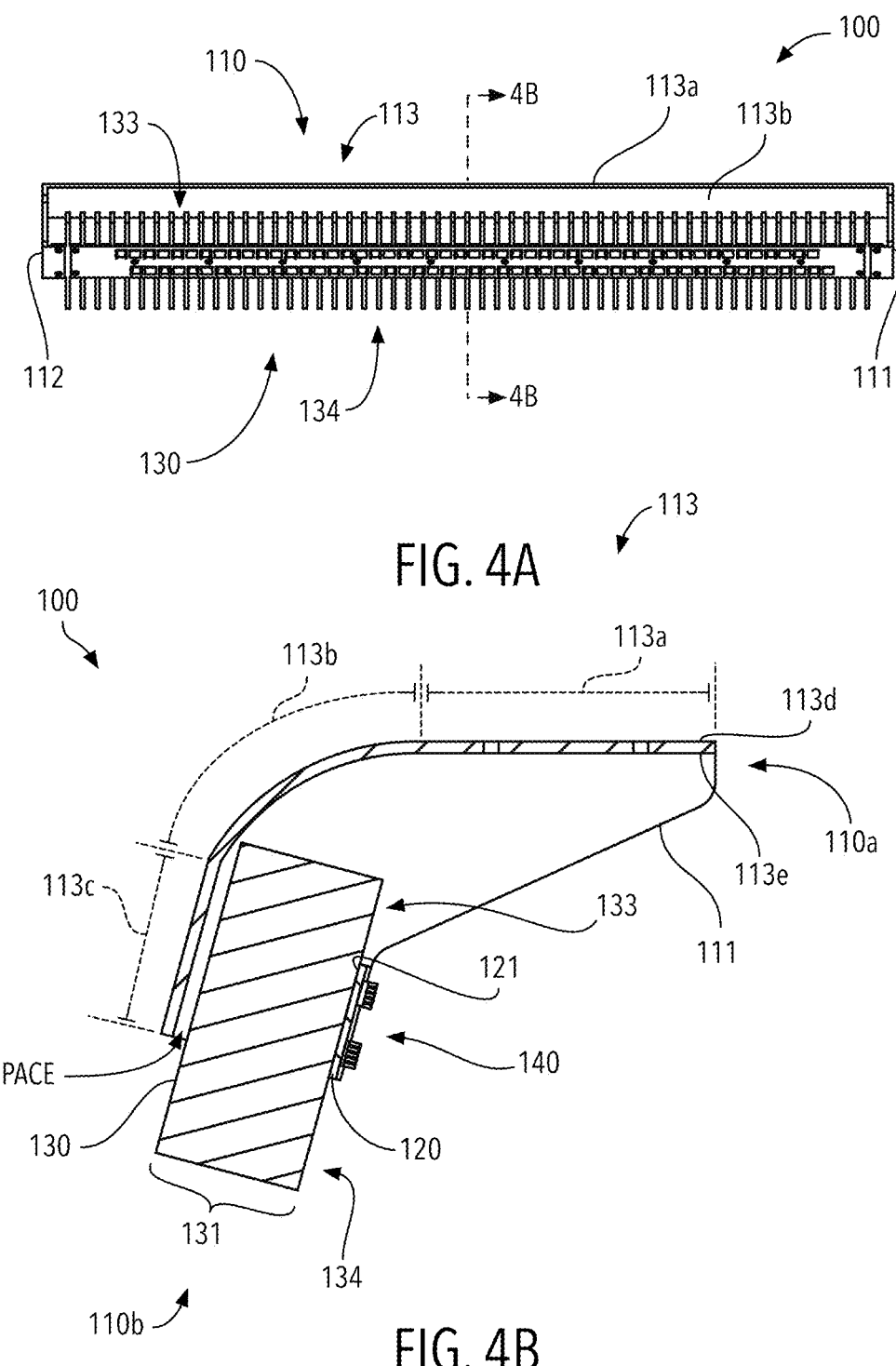
FIG. 4A is a front view of UV-C air scoop apparatus 100 of the present invention.
FIG. 4B is a cross-sectional view of UV-C air scoop apparatus 100 taken generally along line 4B-4B in FIG. 4A.

The following description should be taken in view of FIGS. 4A and 4B. FIG. 4A is a front view of UV-C air scoop apparatus 100 removed from HVAC duct 200 and FIG. 4B is a cross-sectional view taken generally along line 4B-4B in FIG. 4A. Heat sink 130 is arranged on heat sink mounting surface 121 of mounting bracket 120, where mounting bracket 120 is secured to air scoop 110 (shown in FIG. 5). Heat sink 130 comprises plurality of fins 131, where plurality of fins 131 includes upper portion 133 and lower portion 134. Upper portion 133 of plurality of fins 131 is arranged to be disposed within air scoop 110 and lower portion 134 of plurality of fins 131 is arranged to extend outwardly from outlet end 110b, that is, lower portion 134 is outside of air scoop 110. Plurality of fins 131 are preferably radiator fins which are surfaces that extend from heat sink 130 to increase the rate of heat transfer from UV-C air scoop apparatus 100 by increasing convection. It should be appreciated that, in alternative embodiments where increased heat transfer is needed, plurality of fins 131 could also include heat pipes, that is, fully scaled, passive two-phase heat transfer devices that take advantage of a fluid's high heat of vaporization, contained within the heat pipes, to achieve more efficient heat transfer. As shown in FIG. 4B, a space (SPACE) may be present between internal surface 113e and plurality of fins 131.

Air scoop 110 includes air directing portion 113. Air directing portion 113 is arranged to direct incoming air into air scoop 110 at inlet end 110a, over plurality of fins 131 of heat sink 130, and out through outlet end 110b. Air directing portion 113 includes three portions: mounting portion 113a; contoured portion 113b; and, outlet portion 113c. Mounting portion 113a is defined as the area of air scoop 110 that is removably secured to internal surface 210a of top member 210 of HVAC duct 200, as shown in FIGS. 1B and 2B. Mounting portion 113a merges into contoured portion 113b which curves mounting surface 113d and internal surface 113e in a substantially downward configuration, towards heat sink 130 and UV light module 140. Contoured portion 113b merges into outlet portion 113c which terminates at outlet end 110b. Heat sink 130 and UV light module 140 are preferably arranged proximate to outlet portion 113c.

Figure 11:
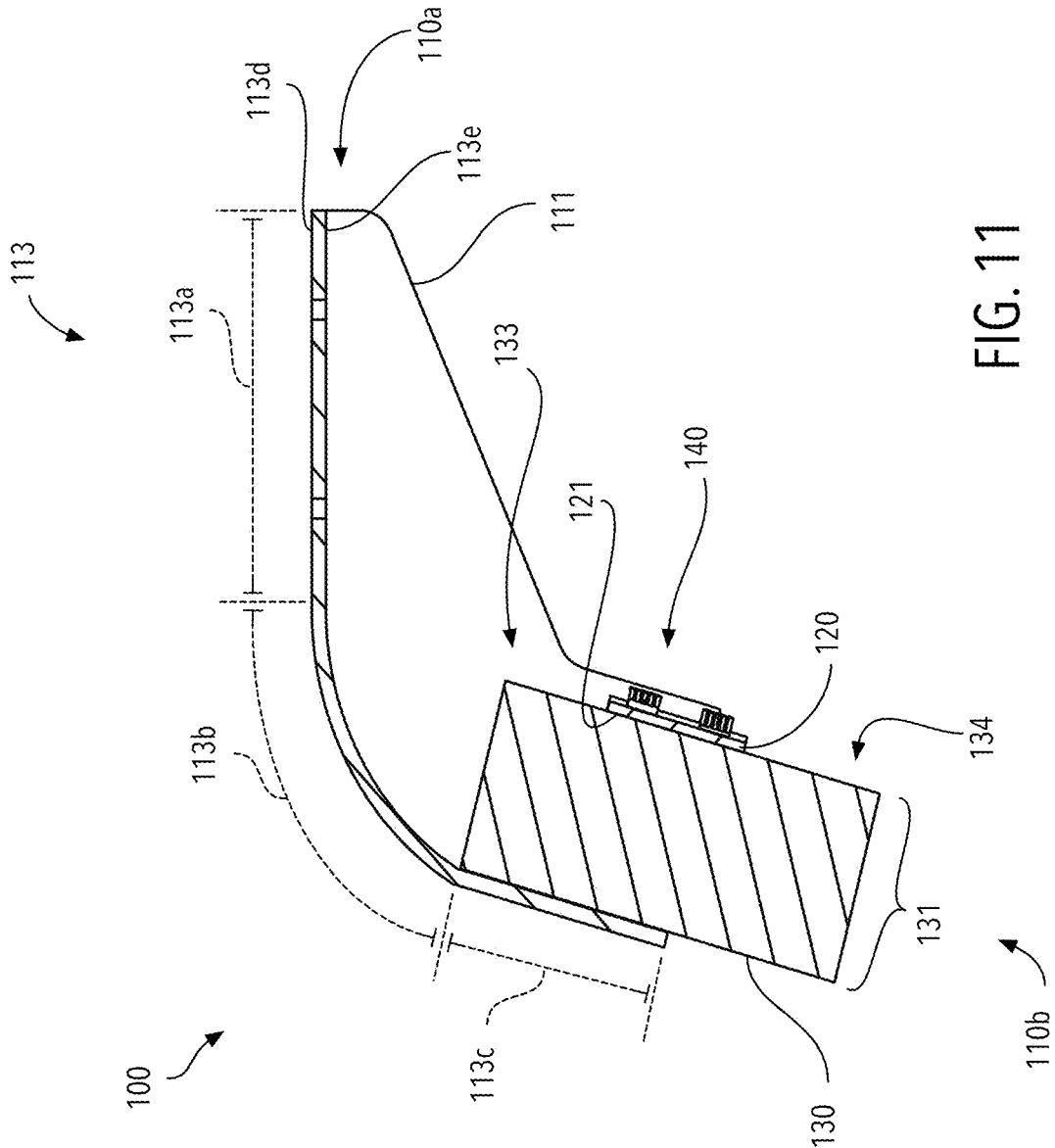

As shown in FIG. 11, which generally illustrates an alternative arrangement of the invention shown in FIG. 4B, specifically, no space (SPACE shown in FIG. 4B) is present between internal surface 113e and plurality of fins 131. This alternative arrangement is generally referred to as a "closed" arrangement. The closed arrangement results in increased air pressure proximate the front of the heat sink, i.e., the surface having the LEDs, thusly creating greater air flow through the heat sink, or the plurality of fins of the heat sink, therefore increasing the temperature mitigation properties of the heat sink. Specifically, the closed arrangement, prevents incoming air from bypassing the plurality of fins, via the space (SPACE) between the fins and the internal surface of the air scoop (shown in FIG. 4B), causing the differential pressure to rise in front of the heatsink (i.e., the surface proximate the LEDs) and rise behind the heatsink, which increases net airflow through the heatsink, thereby generating an appreciable drop in temperature at the LED junction, i.e., UV light module 140.

Figure 5:
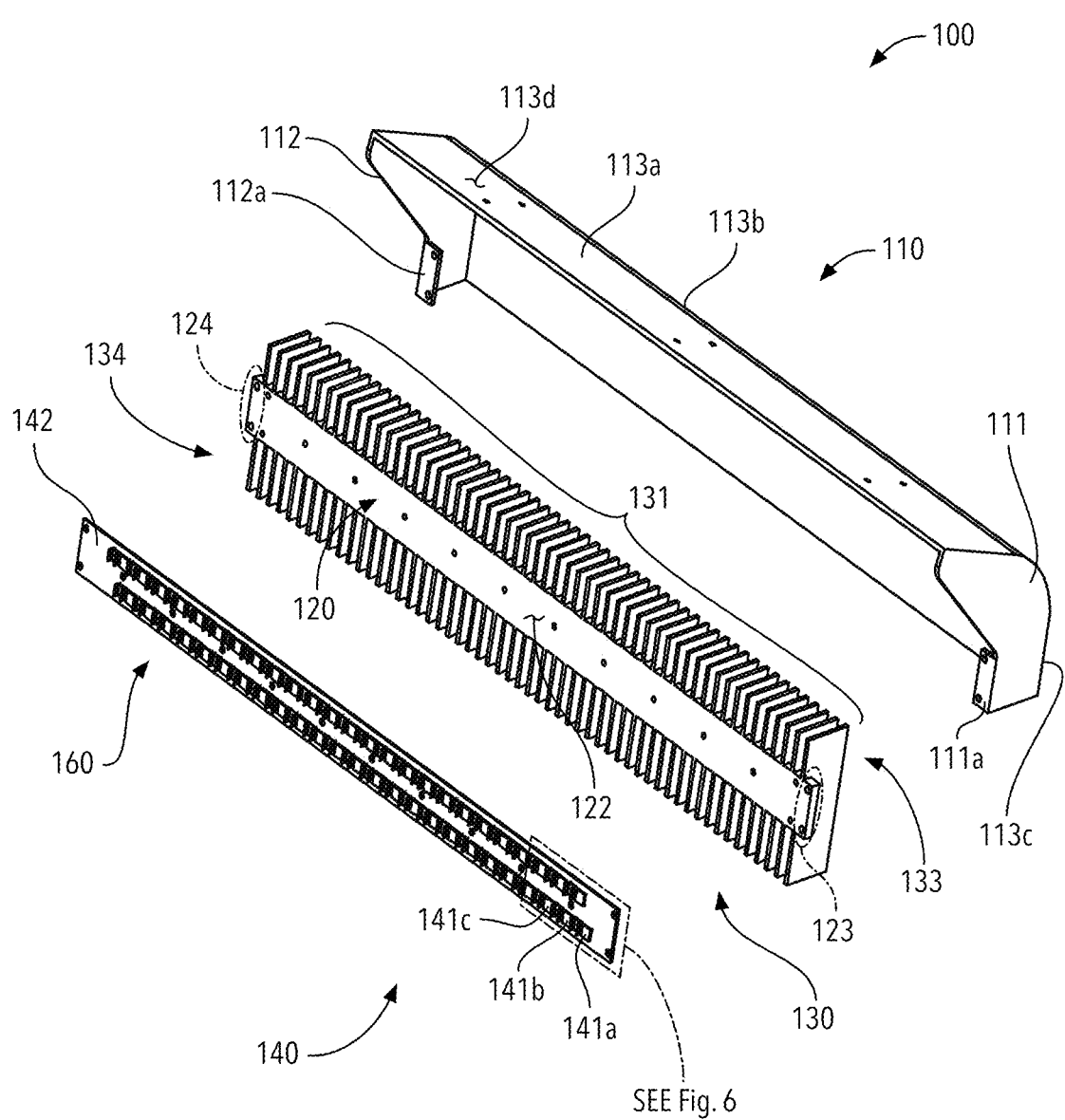
FIG. 5 is an exploded view of UV-C air scoop apparatus 100.

FIG. 5 is an exploded view of UV-C air scoop apparatus 100. Air scoop 110 includes mounting bracket 111a of first side panel 111 and mounting bracket 112 of second side panel 112, both of which extend from the respective side panels. Mounting brackets 111 and 112 are arranged to engage first mounting end 123 and second mounting end 124 of mounting plate 120, preferably via screws, however other acceptable mounting means may be contemplated. Heat sink 130 is arranged on heat sink mounting surface 121 (shown in FIG. 4B) of mounting bracket 120. UV light module 140 is arranged to secure to UV light module mounting surface 122, specifically PCB board 142, preferably via screws, however other acceptable mounting means may be contemplated. Arranged on PCB board 142 are plurality of LED heat sinks 160 and plurality of UV LEDs 141, having individual LED lights 141a, 141b, 141c, etc.

In a preferred embodiment, plurality of LED heat sinks 160 are comprised of copper. Alternatively, plurality of LED heat sinks 160 may be comprised of a copper-nickel combination, stainless steel (e.g., 316, 304, or other suitable stainless steel types), Heresite P413-coated aluminum, E-coated aluminum, aluminum, or other suitable steel alloys.

Plurality of UV LEDs 141 may comprise any suitable LED rated at approximately 270 to 280 nm wavelength. Possible LEDs may include single LEDs, chip-on-board LEDs, LED strip(s), to a complete LED light source. Examples of suitable LEDs are provided by International-Light Technologies, part Nos.: E275-3, E275-3-S, ILT-PWRTYLED.3 W, E275-10, E275-10-S, E275-60-Strip, or ILT-PWR-12600P5. It should be appreciated that the above-identified examples of LEDs are intended to be non-limiting in view of the appending claims.

Figure 6:
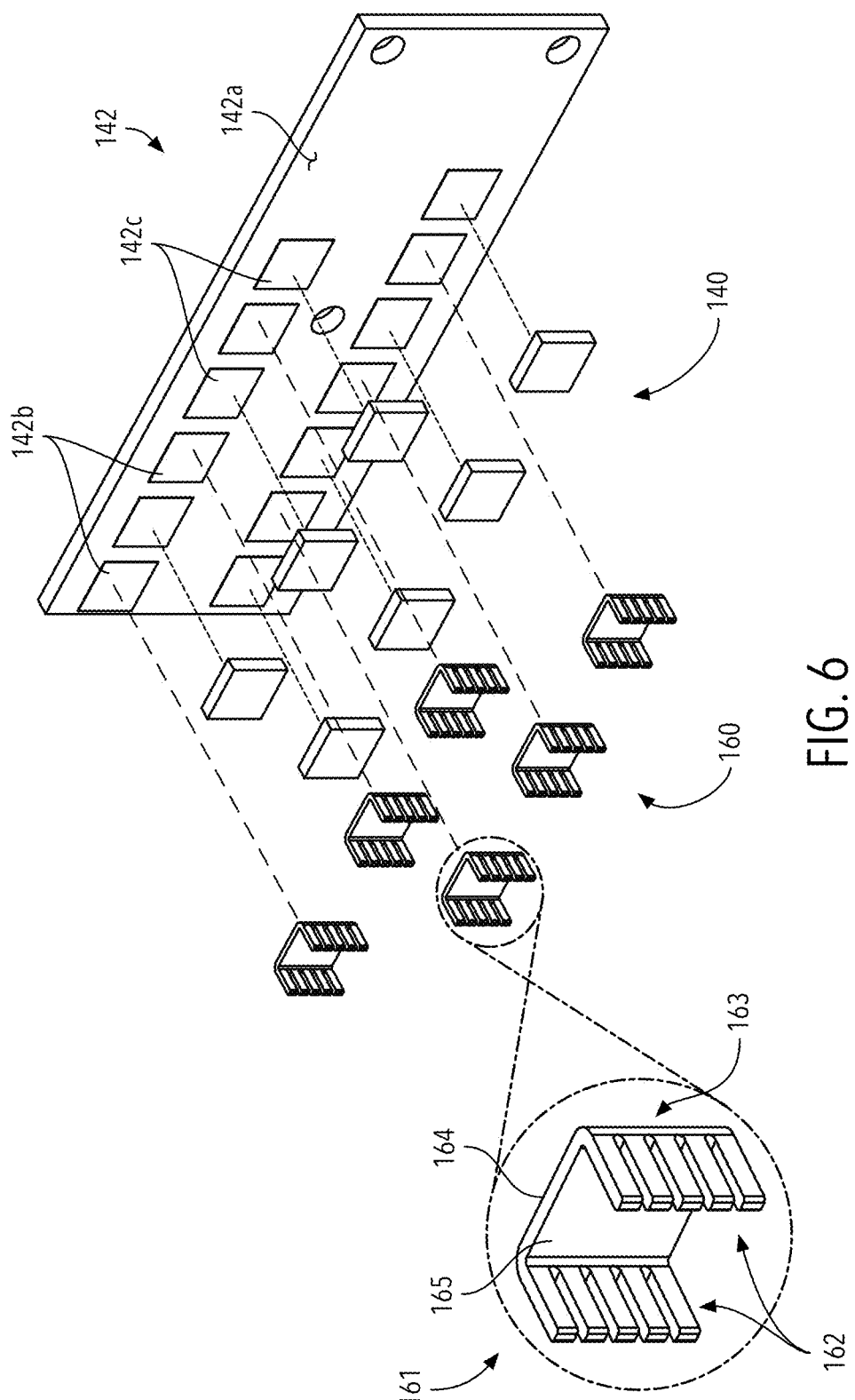
FIG. 6 is a partial exploded view of PCB board 142 taken from FIG. 5, also illustrating an enlarged view of LED heat sink 161.

FIG. 6 illustrates a partial view of PCB board 142 taken from FIG. 5. FIG. 6 also illustrates an enlarged view of LED heat sink 161. Plurality of UV LEDs 141 and plurality of LED heat sinks 160 are arranged on mounting surface 142a of PCB board 142. Mounting surface 142 includes a plurality of inputs, inputs for LED lights 142b and inputs for heat sinks 142c. It should be appreciated that inputs 142b and 143c are in electronic and powered communication with PCB board 142, where PCB board 142 is in electronic and powered communication with control module 150 (shown in FIGS. 7A-7C). Inputs 142b and 142c are arranged to accept an LED light and an LED light heat sink. It should also be appreciated that inputs 142c may be arranged as mounting positions for plurality of LED heat sinks 160 and may not be in electronic and powered communication with PCB board 142.

Individual LED light heat sink 161 of plurality of LED heat sinks 160 are arranged to collectively provide additional heat dissipation of the heat generated by plurality of UV LEDs 141 and heat from incoming air traveling towards and through HVAC duct 200, in conjunction with heat sink 130 (shown in FIG. 5). Individual LED light heat sink 161 generally comprises base 163 and plurality of fins 162. Plurality of fins 162 are arranged to extend from base 163. Plurality of fins 162 are preferably radiator fins which are surfaces that extend from Individual LED light heat sink 161 to increase the rate of heat transfer by increasing convection. Mounting surface 164 of base 163 is arranged to engage one of inputs for heat sinks 142c on PCB board 142 and external surface 165 of base 163 is arranged opposite from mounting surface 164.

Figures 7A, 7B:
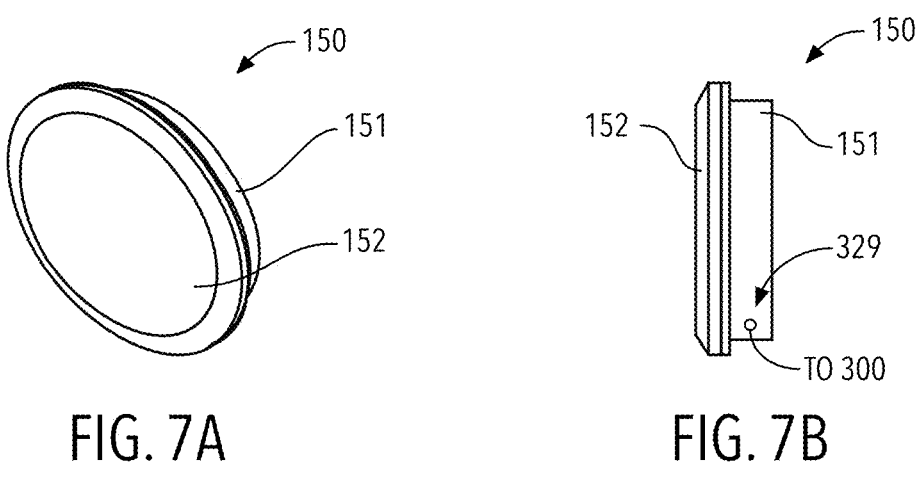
FIG. 7A is a perspective view of control module 150.
FIG. 7B is a side view of FIG. 7A.
Figure 7C:
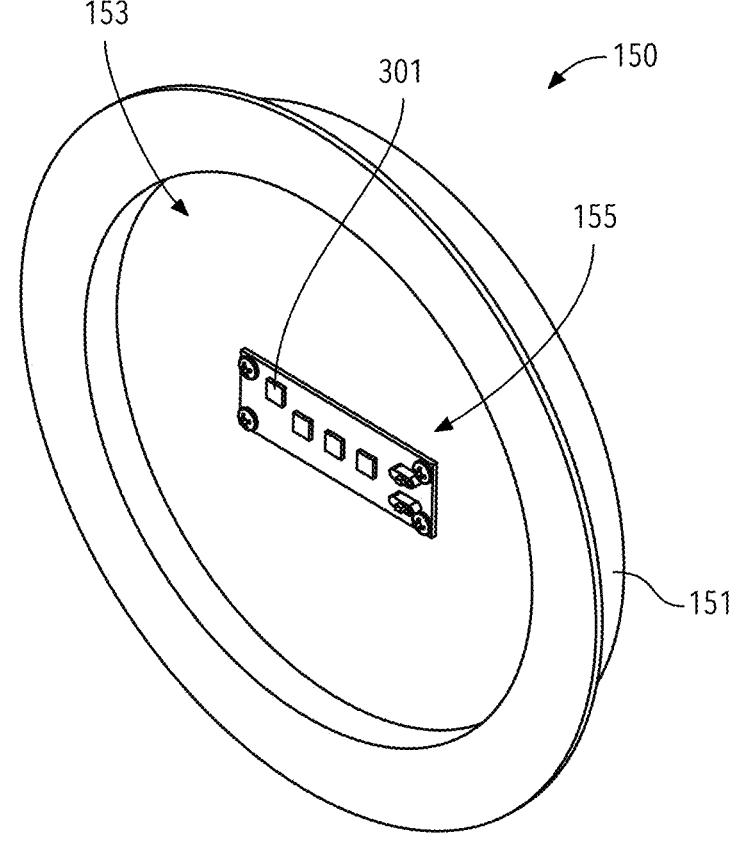
FIG. 7C is a perspective view of control module 150 without cover 152.

The following description should be taken in view of FIGS. 7A through 7C. FIG. 7A illustrates a perspective view of control module 150, FIG. 7B illustrates a side view of control module 150, and FIG. 7C illustrates a perspective view of control module 150 without cover 152. Control module 150 is arranged such that it will receive power from an external power source and communicate the power to UV light module 140. UV-C air scoop apparatus 100 is arranged to be connected to a power source, preferably an alternating voltage supply (VAC) and is also arranged to provide a conversion to a direct voltage supply (VAC to VDC) conversion internally in addition to a VAC bypass to allow VAC current to power components of the present invention in addition to the VDC current. Control module 150 includes internal cavity 153 within main body 151 which is sealed by cover 152. Disposed within internal cavity 153 is control board 155 which is arranged to execute and control UV-C air scoop apparatus 100 and the external components, discussed infra. Control module 150 receives power from power source 300 at 2-pin connector 329, which power will be VAC which is converted by power source 300 to VDC. Also shown in FIG. 7C is sensor board 301, shown in greater detail in FIG. 8 and discussed further, infra.

Figure 8:
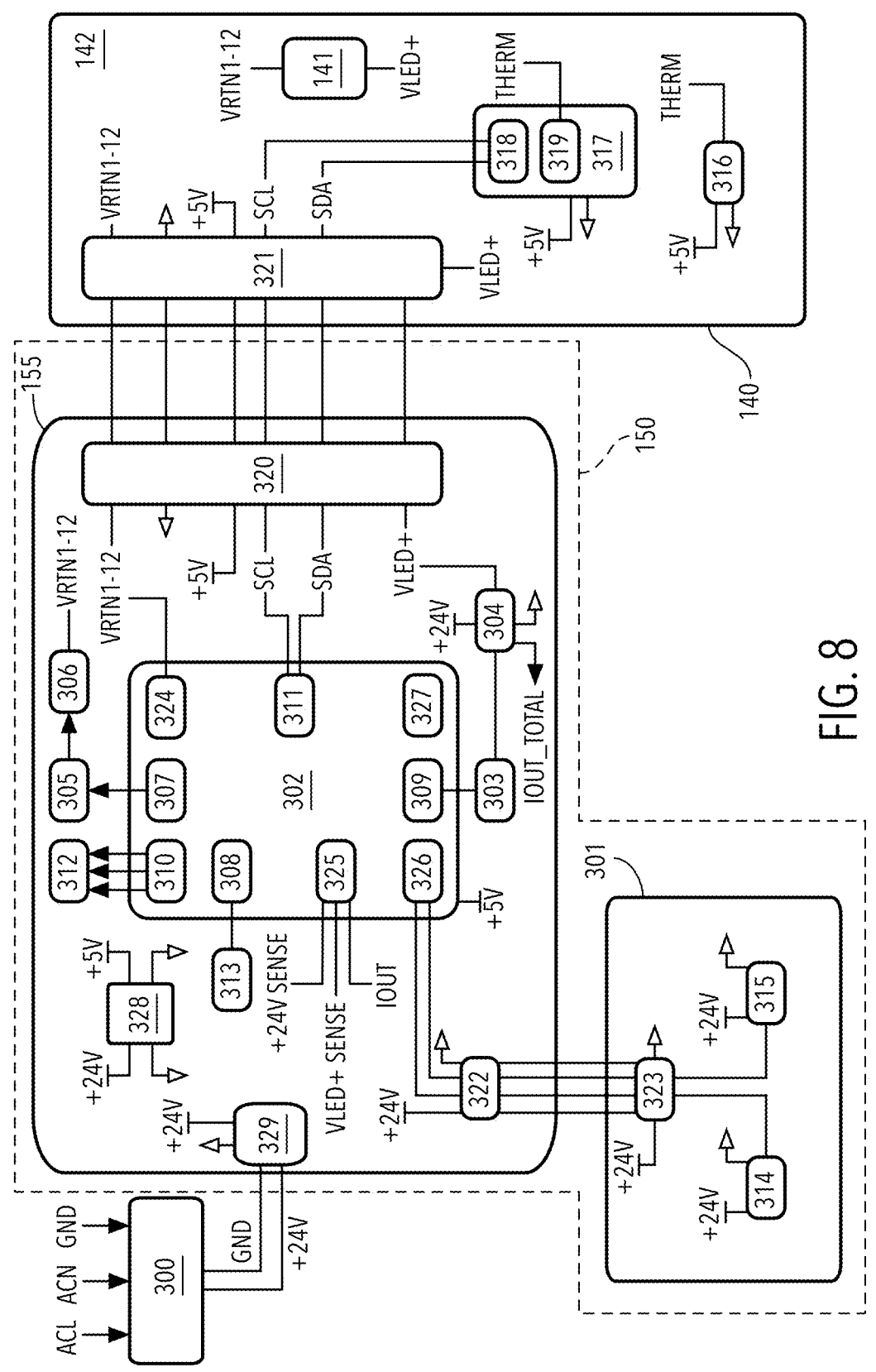
FIG. 8 is a high-level circuit schematic of the present invention.

FIG. 8 is a high-level circuit schematic of the components of UV-C air scoop apparatus 100. Specifically, FIG. 8 illustrates control module 150, control board 155, UV light module 140, sensor board 301, and power source 300. Power source 300 is preferably arranged to accept VAC and convert the VAC current to VDC current. In a preferred embodiment, power source 300 accepts an approximate minimum of 120 VAC 60 Hz with approximately 10% variation. In alternative embodiments, power source 300 would be capable of a universal input range to cover installation of UV-C air scoop apparatus 100 in all regions, e.g., 90 VAC to 277 VAC at both 60 Hz and 50 Hz. Power source 300 preferably provides an output voltage of 24 VDC+/−5% under all load conditions. Depending on the wattage of plurality of UV LEDs 141, the output power rating of power source 300 may vary from 100 W-300 W for plurality of UV LEDs 141 having an approximate wattage of 75 W-225 W. Control board 155 also includes buck regulator 328, which is arranged to step down the 24 VDC to approximately 5 VDC to provide 5 VDC power to selected components within control board 155 and/or UV light module 140.

Microcontroller 302 in a preferred embodiment includes three (3) PWMs (pulse width modulated signal generator) 307, 308, and 309. PWMs 307, 308, and 309 are connected to low pass filter 305, alarm 313, and low pass filter 303, respectively.

Microcontroller 302 in a preferred embodiment may be an AVR® AVR32DA48, which includes the AVR® processor with hardware multiplier, running capability up to 24 MHz with 32 KB Flash, 4 KB SRAM and 512 bytes of EEPROM in 48-pin packages having TQFP and VQFN package options. It should also be appreciated that microcontroller 302 may comprise any alternative microcontroller that can provide the functionality described herein.

In a preferred embodiment, microcontroller 302 will include a dedicated communication interface to printed circuit board (PCB) MCU 317 of UV light module 140, via I2C 311 (I2C 311 to 14-pin connector 320 to 14-pin connector 321 to I2C 318 of PCB MCU 317). It should also be appreciated that UART (universal asynchronous receiver-transmitter) 327 may be arranged to allow for external communication from microcontroller 302, e.g., to an external computing device such as a cell phone. PCB MCU 317 is primarily arranged to log faults related to plurality of UV LEDs 141, discussed further infra, which are communicated to microcontroller 302. Depending on the particular fault encountered, either alarm 313 or indicator 312, or both, will be activated. Indicator 312 is arranged to provide a visual alarm, e.g., indicator light, and is connected to PWM x3 310 of microcontroller 302. Indicator 312 in a preferred embodiment is arranged to be able to display a plurality of colors associated with a plurality of different faults. Alarm 313 is arranged to provide an audio alarm and is connected to PWM 308.

In a preferred embodiment, PCB MCU 317 may be an AVR® ATtiny404 microcontroller, which includes 8-bit AVR® processor with a hardware multiplier, with a running capability up to 20 MHz and 4 KB Flash, 256B SRAM, and 128B of EEPROM in a 14-pin package. It should also be appreciated that PCB MCU 317 may comprise any alternative microcontroller that can provide the functionality described herein.

Adjustable boost converter 304 is connected to low pass filter 303 and PWM 309 of microcontroller 302. Adjustable boost converter 304 is arranged to supply any voltage necessary to begin driving current through plurality of UV LEDs 141, until a maximum voltage is reached. Adjustable boost converter 304 is preferably arranged to have an approximate maximum output voltage of 60V+/−5%, however it should be appreciated that the approximate maximum output voltage is merely exemplary and one having ordinary skill in the art would appreciate possible alternatives in the practice of the present invention. Microcontroller 302 is arranged to control the output of adjustable boost converter 304 to preferably maintain an approximate minimum of 250 mV as the lowest return voltage of plurality of UV LEDs 141—ensuring maximum efficiency and the lowest heat generation from linear current control 306, however it should be appreciated that the approximate lowest return voltage is merely exemplary and one having ordinary skill in the art would appreciate possible alternatives in the practice of the present invention.

Linear current control 306 is connected to low pass filter 305 and PWM 307 of microcontroller 302. Linear current control 306 is arranged to regulate the current in each LED of plurality of UV LEDs 141 to maintain a high degree of current accuracy in each of the individual LEDs and to protect the individual LEDs. PWM 307 of microcontroller 302 is arranged as a single filtered PWM output to each linear current control circuit of the linear current control 306, driving each of individual current control circuits with the same reference. Linear current control 306 is arranged to maintain an approximate LED current within 10 mA of the reference input, where the reference input is programmably adjustable via microcontroller 302.

Control board 155 within control module 150 is arranged to control the current through UV light module 140 and is further arranged to provide the on/off protocol of plurality of UV LEDs 141 of UV light module 140 based whether approximately 200 fpm, or greater, of air is flowing through an HVAC duct. The on/off protocol is primarily conducted via microcontroller 302 which is determined by calculating approximate airflow from communicated temperature readings from NTC thermistor and resistor 314 (heat-source temperature sensor and external heat source) and NTC thermistor 315 (ambient temperature sensor). In a preferred embodiment the on/off protocol of microcontroller 302 is arranged to turn on plurality of UV LEDs 141 of UV light module 140 when approximately 200 fpm, or greater, airflow is detected and is arranged to off plurality of UV LEDs 141 of UV light module 140 when approximately 175 fpm, or less, airflow is detected.

Negative temperature coefficient (NTC) thermistor and resistor 314 and NTC thermistor 315 are both arranged on sensor board 301. Sensor board 301 is connected to control board 155 via 4-pin connectors 323 and 322, specifically 4-pin connector is connected to ADC x2 326 of microcontroller 302. 4-pin connectors 323 and 322 also connect NTC thermistor and resistor 314 and NTC thermistor 315 to control board 155. NTC thermistor and resistor 314 are arranged such that the resistor will be used as the heat source in which NTC thermistor will measure the heat emitted therefrom. NTC thermistor 315 is arranged to measure the ambient temperature which measurements are thereby communicated to microcontroller 302 for comparison. By comparing the ambient temperature reading of NTC thermistor 315 and the temperature reading of NTC thermistor and resistor 314, microcontroller 302 can decide as to whether airflow is present and thereby initiate the on/off protocol, e.g., when the temperature readings of 314 and 315 are closer, airflow is present and when the temperature readings of 314 and 315 are farther apart, airflow is not present.

UV light module 140 includes PCB board 142, having plurality of UV LEDs 141 arranged thereon and connected thereto. Control board 155 is connected to PCB board 142 via 18-pin connectors 320 and 321, respectively. This arrangement allows PCB board 142 to be easily replaced in the event it is damaged. 18-pin connector 320 is arranged to be connected to adjustable boost converter 304, input ADC x12 324 (analog-to-digital converter) of microcontroller 302, and I2C 311 (inter-integrated circuit) of microcontroller 302, thereby connecting the aforementioned components to UV light module 140. PCB board 142 includes PCB MCU 317 which includes ADC 319 and I2C 318. Specifically, I2C 318 is connected to 18-pin connector 321, 18-pin connector 321 is connected to 18-pin connector 320, and 18-pin connector 320 is connected to microcontroller 302 at I2C 311—connecting microcontroller 302 to PCB MCU 317 for communication relay. PCB board 142 also includes NTC thermistor 316 that is arranged to provide microcontroller 302 with temperature readings of PCB board 142 and/or plurality of LEDs 141 for safety shutoff purposes.

ADC x3 325 (analog-to-digital converter with three inputs) of microcontroller 302 has three inputs that arranged to monitor values for the fault-logging protocol of microcontroller 302. The three inputs from ADC x3 325 are +24V SENSE, VLED+SENSE, and IOUT. The first input, +24V SENSE is arranged to monitor power supply 300, specifically the main power coming from power supply 300 into control board 155. In a preferred embodiment, a target range of power is programmed into microcontroller 302 and if the +24V SENSE input of ADC x3 325 detects incoming power that is not within the target range, microcontroller 302 will log the detection and determine based on the detected range whether to shut of plurality of LEDs 141. The second input, VLED+SENSE is arranged to monitor the output provided by adjustable boost converter 304. Boost converter 304 is arranged to have a preselected output, such that if VLED+ SENSE detects an output different than the preselected output, microcontroller 302 may be programmed to turn off plurality of LEDs 141 and/or trigger an alarm through indicator 312 and/or alarm 313. The third input, IOUT is arranged to monitor the total current through plurality of LEDs 141. In a preferred embodiment, a target range of current is programmed into microcontroller 302 and if IOUT input of ADC x3 325 detects current through plurality of LEDs 141 that is not within the target range, microcontroller 302 will log the detection and determine which of the VRTN1-12 signals is out of the range and shut that individual LED string off.

Figure 9:
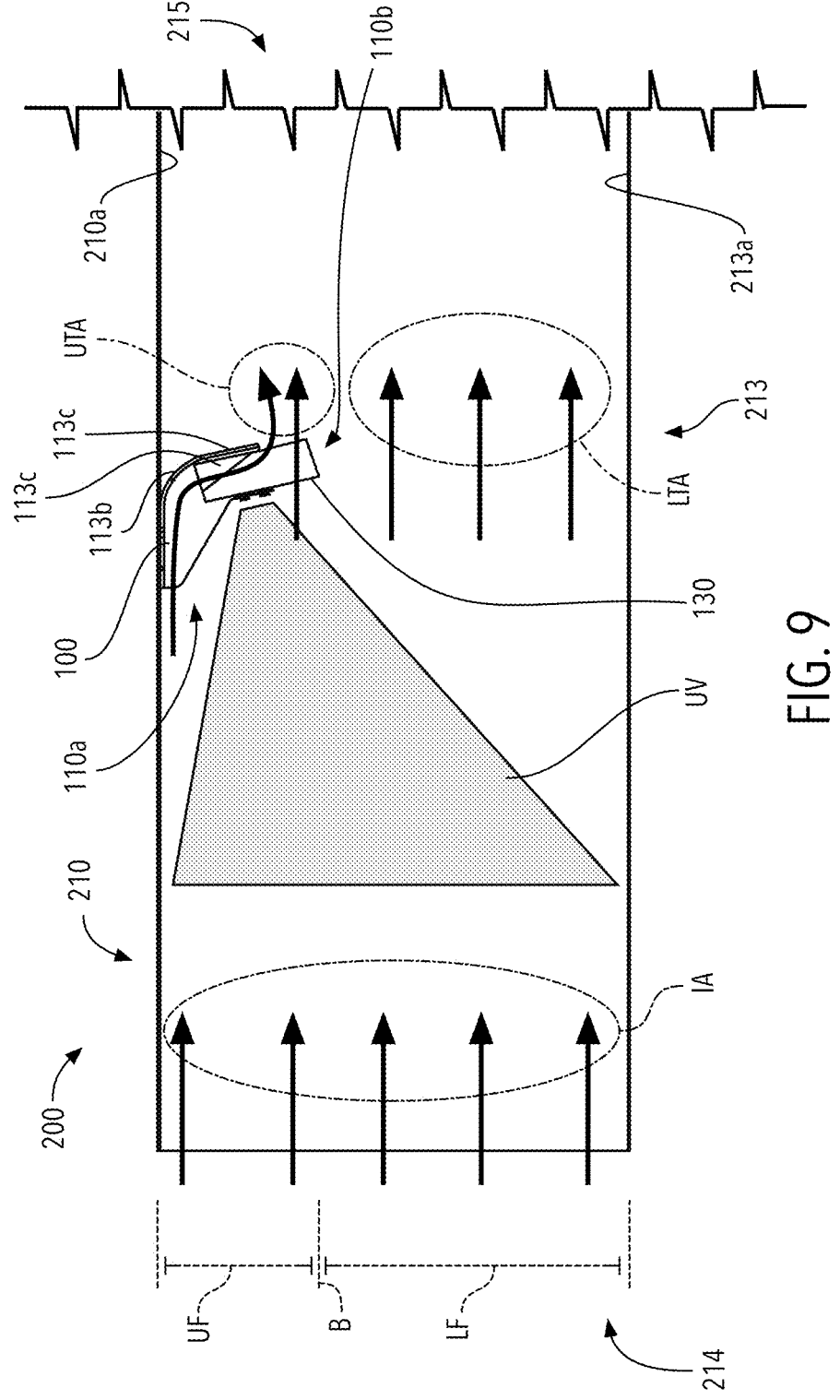
FIG. 9 is a cross-sectional view of the HVAC duct taken generally along line 2B-2B in FIG. 2A specifically showing air flow pathways through HVAC duct 200.

FIG. 9 is a cross-sectional view of the present invention taken generally along line 2B-2B in FIG. 2A specifically showing air flow pathways through HVAC duct 200 with UV-C air scoop apparatus 100 installed therein. Incoming airflow IA comes from inlet end 214 of HVAC duct 200. Incoming airflow IA is treated by ultraviolet light UV emitted from UV-C air scoop apparatus 100. Ultraviolet light UV emitted from UV-C air scoop apparatus 100 treats incoming airflow IA prior to reaching UV-C air scoop apparatus 100. Once incoming airflow IA reaches inlet end 110*a* of UV-C air scoop apparatus 100, it is bifurcated B into upper flow UF and lower flow LF. As discussed supra, UV-C air scoop apparatus 100 includes mounting portion 113*a*, contoured portion 113*b*, and outlet portion 113*c* of air directing portion 113. Upper flow UF of incoming airflow IA, that has been treated by ultraviolet light UV, does two things, a portion of incoming airflow IA enters mounting portion 113*a*, contoured portion 113*b*, and outlet portion 113*c* of air directing portion 113, which directs the treated incoming airflow IA over heat sink 130 to assist in the heat mitigation of UV-C air scoop apparatus 100, while the other portion of incoming air IA passes directly through the lower fins of heat sink 130—also assisting in the heat mitigation of UV-C air scoop apparatus 100. Upper treated airflow UTA and lower treated airflow LTA will both continue to flow through duct 200 towards outlet end 215.

Figure 10:
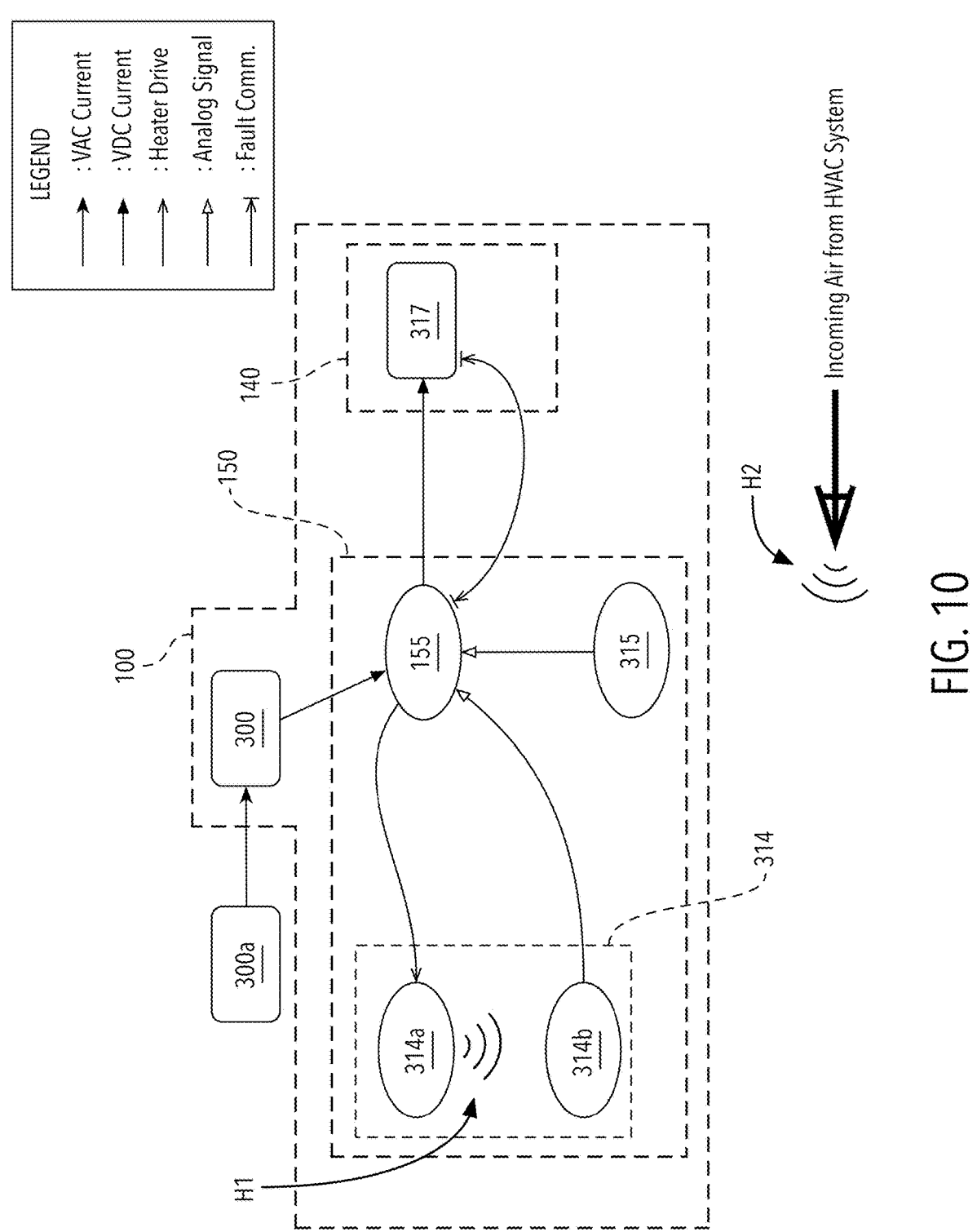
FIG. 10 is a high-level flow diagram of the operation of the present invention; and, FIG. 11 is a cross-sectional view taken generally along line 4B-4B in FIG. 4A.

FIG. 10 is high-level flow diagram of the on/off protocol of UV-C air scoop apparatus 100. External VAC power source 300*a* sends VAC current to power source 300. Power source 300 converts/rectifies the VAC current to VDC current which powers UV-C air scoop apparatus 100 and provides power to all of control module 150 (shown providing power to control board 155). FIG. 10 illustrates UV light module 140 and PCB MCU 317 receiving VDC from control board 155. The heater drive is sent from control board 155 to NTC thermistor and resistor 314, specifically to resistor 314*a*. Resistor 314*a* generates heat H1 which is detected by NTC thermistor 314*b* to be communicated from NTC thermistor and resistor 314 to control board 155. NTC thermistor 315 detects heat/airflow temperature H2 from incoming air from the HVAC system. NTC thermistor 315 communicates the temperature reading of H2 to control board 155. Control board 155 measures the differential between NTC thermistor 315 and NTC thermistor and resistor 314 to determine if airflow is present in the HVAC duct, i.e., smaller differential equates to airflow and larger differential equates to no airflow. PCB MCU 317 also cross-communicates with control board 155 any fault condition that is either from UV light module 140 or control module 150, which fault is stored in the memory of the microcontroller of control module 150.

Fault Monitoring

The following description should be taken in view of FIG. 8 and relates to the fault monitoring recorded by microcontroller 302 or PCB MCU 317, or both.

An open UV-C LED fault would occur if a single LED of plurality of LEDS 141 was to open. If this fault is detected, a signal will be sent to microcontroller 302 and the fault will be logged into the memory of microcontroller 302 and will also indicate the failure via alarm 313 and indicator 312.

A shorted UV-C LED fault would occur if a single LED of plurality of LEDS 141 was to short out. If this fault is detected, a signal will be sent to microcontroller 302 and the fault will be logged into the memory of microcontroller 302 and will also indicate the failure via alarm 313 and indicator 312.

An LED current fault would occur if a single LED of plurality of LEDs 141 has a current of more than a 10% deviation from the driven value for longer than approximately 100 ms. If this fault is detected, a signal will be sent to microcontroller 302 and the fault will be logged into the memory of microcontroller 302 and will also indicate the failure via alarm 313 and indicator 312.

A Boost Converter fault would occur if the output of boost converter 304 is greater than approximately 24V +5%. If this fault is detected, a signal will be sent to microcontroller 302 and the fault will be logged into the memory of microcontroller 302 and will also indicate the failure via alarm 313 and indicator 312.

A High Voltage Input fault would occur if the input voltage to control board 155 is greater than approximately 24V +5%. If this fault is detected, a signal will be sent to microcontroller 302 and the fault will be logged into the memory of microcontroller 302 and will also indicate the failure via alarm 313 and indicator 312.

A Low Voltage Input fault would occur if the input voltage to control board 155 is less than approximately 24V-5%. If this fault is detected, a signal will be sent to microcontroller 302 and the fault will be logged into the memory of microcontroller 302 and will also indicate the failure via alarm 313 and indicator 312.

An Airflow Detection fault would occur if NTC thermistor 315 (the ambient air thermometer) detects greater than approximately 85° C., or less than approximately –20° C. If this fault is detected, a signal will be sent to microcontroller 302 and the fault will be logged into the memory of microcontroller 302 and will also indicate the failure via alarm 313 and indicator 312. Airflow detection fault is also if the thermistor of NTC thermistor and resistor 314 has a temperature greater than approximately 10° C. less than the temperature detected by thermistor 315, microcontroller 302 will be communicated the fault which will be logged into the memory of microcontroller 302 and will also indicate the failure via alarm 313 and indicator 312.

An External MCU Communication fault would occur if communication between microcontroller 302 and PCB board MCU is lost. If this fault is detected, microcontroller 302 and/or PCB MCU 317 will log the fault into their respective memories while also indicating the failure via alarm 313 and indicator 312.

An LED Stick Overtemperature fault would occur if NTC thermistor 316 detects a temperature greater than approximately 60° C., in which case microcontroller 302 will turn off plurality of LEDs 141 and microcontroller 302 and/or PCB MCU 317 will log the fault into their respective memories while also indicating the failure via alarm 313 and indicator 312.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

REFERENCES NUMERALS

100 UV-C air scoop apparatus
110 Air scoop
110a Inlet end of air scoop 110
110b Outlet end of air scoop 110
111 First side panel of air scoop 110
111a Mounting bracket of first side panel 111
112 Second side panel of air scoop 110
112a Mounting bracket of second side panel 112
113 Air directing portion of air scoop 110
113a Mounting portion of air directing portion 113
113b Contoured portion of air directing portion 113
113c Outlet portion of air directing portion 113
113d Mounting surface of mounting portion 113a
113e Internal surface of air directing portion 113
120 Mounting plate
121 Heat sink mounting surface of mounting plate 120
122 UV light module mounting surface of mounting plate 120
123 First mounting end of mounting plate 120
124 Second mounting end of mounting plate 120
130 Heat sink of air scoop 110
131 Plurality of fins of heat sink 130

132 Mounting surface of heat sink 130
133 Upper portion of plurality of fins 131
134 Lower portion of plurality of fins 131
140 UV light module of air scoop 110
141 Plurality of UV LEDs
141a, 141b, . . . Individual UV LEDs
142 PCB board of UV light module 140
142a Mounting surface of PCB board 142
142b Inputs for LED light
142c Inputs for LED heat sinks
150 Control module
151 Main body of control module 150
152 Cover of main body 151
153 Internal cavity of main body 151
155 Control board
160 Plurality of LED heat sinks
161 LED heat sink of plurality of LED heat sinks 160
162 Plurality of fins of LED heat sink 161
163 Base of LED heat sink 161
164 Mounting surface of base 163
165 External surface of base 163
200 HVAC duct
210 Top member of duct 200
210a Internal surface of top member 210
211 First side member of duct 200
212 Second side member of duct 200
212a Internal surface of second side member 212
212b External surface of second side member 212
213 Bottom member of duct 200
213a Internal surface of bottom member 213
214 Inlet end of duct 200
215 Outlet end of duct 200
300 Power source
300a External VAC power source
301 Sensor board
302 Microcontroller
303 Low pass filter
304 Adjustable boost converter
305 Low pass filter
306 Linear current control
307 Pulse width modulated signal generator (PWM)
308 PWM
309 PWM
310 PWM x3
311 Inter-integrated circuit (I2C)
312 Indicator
313 Alarm
314 NTC thermistor and resistor
314a Resistor
314b NTC thermistor
315 NTC thermistor
316 NTC thermistor
317 PCB (printed circuit board) MCU
318 I2C
319 Analog-to-digital converter (ADC)
320 18-pin connector
321 18-pin connector
322 4-pin connector
323 4-pin connector
324 ADC x12
325 ADC x3
326 ADC x2
327 Universal asynchronous receiver transmitter (UART)
328 5V buck regulator
329 2-pin connector
B Bifurcation plane of UV-C air scoop apparatus 100
H1 Heat H2 Heat/Airflow temperature
IA Incoming air
LF Lower flow of incoming air from bifurcation B
LTA Lower treated air
UF Upper flow of incoming air from bifurcation B
UTA Upper treated air
UV Ultraviolet light
What is claimed is:

1. An air sanitizing apparatus arranged within an HVAC duct, comprising:

an air scoop, said air scoop arranged on a surface of said HVAC duct, said air scoop having an inlet end and an outlet end, said air scoop having a bracket extending distally from said air scoop;

a UV light module, said UV light module secured to said bracket, said UV light module having a temperature sensor;

a heat sink, said heat sink secured to said UV light module and proximate said outlet end; and, a control board, said control board in communication with said UV light module, said control board having a microprocessor in communication with an ambient temperature sensor and a heat-source temperature sensor proximate an external heat source, said microprocessor in communication with said temperature sensor of said UV light module.

2. The air sanitizing apparatus arranged within said HVAC duct recited in claim 1, wherein said UV light module is secured to a PCB (printed circuit board), said UV light module includes a plurality of UV LEDs, each of said plurality of UV LEDs are configured to emit UV-C.

3. The air sanitizing apparatus arranged within said HVAC duct recited in claim 1, wherein said heat sink further comprises:

a plurality of radiator fins arranged to extend beyond UV light module, said plurality of radiator fins have an upper portion and a lower portion, wherein said upper portion and said lower portion of said plurality of radiator fins are secured to said bracket and are further arranged perpendicularly to a pair of mounting faces of said bracket, wherein said upper portion of said plurality of radiator fins is disposed within said air scoop and said lower portion of said plurality of radiator fins extend past said outlet end of said air scoop.

4. The air sanitizing apparatus arranged within said HVAC duct recited in claim 2, wherein said UV light module further comprises a plurality of individual heat sinks secured to said PCB, each of said plurality of individual heat sinks is disposed adjacent to each of said plurality of UV LEDs.

5. The air sanitizing apparatus arranged within said HVAC duct recited in claim 1, wherein said air scoop is arranged to partially obstruct air passing through said duct and direct the obstructed air over said heat sink.

6. The air sanitizing apparatus arranged within said HVAC duct recited in claim 1, wherein when said ambient temperature sensor and said heat-source temperature sensor collect temperatures that are closer in degrees said microcontroller communicates to said UV light module to turn on.

7. The air sanitizing apparatus arranged within said HVAC duct recited in claim 6, wherein when said ambient temperature sensor and said heat-source temperature sensor collect temperatures that are farther in degrees said microcontroller communicates to said UV light module to turn off.

8. The air sanitizing apparatus arranged within said HVAC duct recited in claim 1, wherein said control board is housed in a control module, said control module arranged on said HVAC duct, said control module in electrical communication with an external power source, said control module in electrical communication with said UV light module.

9. A method of sanitizing air flow within an HVAC duct, comprising the steps of:

exposing incoming air within the HVAC duct to UV light with the apparatus recited in claim 1;

bifurcating said incoming air with the air scoop of the apparatus; and, directing said bifurcated air with the air scoop to the heat sink of the apparatus.

10. An air sanitizing apparatus arranged within an HVAC duct, comprising:

an air scoop, said air scoop arranged on a surface of said HVAC duct, said air scoop having an inlet end and an outlet end, said air scoop having a bracket extending distally from said air scoop;

a UV light module, said UV light module secured to said bracket, said UV light module having a temperature sensor;

a heat sink, said heat sink secured to said UV light module and proximate to said outlet end; and, a control board, said control board in communication with said UV light module, said control board having a microprocessor in communication with an ambient temperature sensor and a heat-source temperature sensor arranged proximate to an external heat source, said microprocessor in communication with said temperature sensor of said UV light module, wherein said air scoop is arranged to partially obstruct air passing through said duct and direct the obstructed air over said heat sink, wherein when said ambient temperature sensor and said heat-source temperature sensor collect temperatures that are closer in degrees said microcontroller communicates to said UV light module to turn on.

11. The air sanitizing apparatus arranged within said HVAC duct recited in claim 10, wherein said UV light module is secured to a PCB (printed circuit board), said UV light module includes a plurality of UV LEDs, each of said plurality of UV LEDs are configured to emit UV-C, wherein said air scoop is arranged to partially obstruct air passing through said duct and direct the obstructed air over said heat sink.

12. The air sanitizing apparatus arranged within said HVAC duct recited in claim 11, wherein said UV light module further comprises a plurality of individual heat sinks secured to said PCB, each of said plurality of individual heat sinks is disposed adjacent to each of said plurality of UV LEDs.

13. The air sanitizing apparatus arranged within said HVAC duct recited in claim 10, wherein said heat sink further comprises:

a plurality of radiator fins arranged to extend beyond UV light module, said plurality of radiator fins have an upper portion and a lower portion, wherein said upper portion and said lower portion of said plurality of radiator fins are secured to said bracket and are further arranged perpendicularly to a pair of mounting faces of said bracket, wherein said upper portion of said plurality of radiator fins is disposed within said air scoop and said lower portion of said plurality of radiator fins extend past said outlet end of said air scoop.

14. An air sanitizing apparatus arranged within an HVAC duct, comprising:

an air scoop having an inlet end and an outlet end, said air scoop having a bracket extending distally from said air scoop;

a UV light module mounted on a PCB (printed circuit board), said PCB secured to said bracket, said UV light module having a temperature sensor, said UV light module having a plurality of individual heat sinks arranged thereon;

an air scoop heat sink, said air scoop heat sink secured to said UV light module and proximate to said outlet end; and, a control board, said control board in communication with said UV light module, said control board having a microprocessor in communication with an ambient temperature sensor and a heat-source temperature sensor arranged proximate to an external heat source, said microprocessor in communication with said temperature sensor of said UV light module.

15. The air sanitizing apparatus arranged within said HVAC duct recited in claim 14, wherein said air scoop arranged on a surface of said HVAC duct.

16. The air sanitizing apparatus arranged within said HVAC duct recited in claim 14, wherein said air scoop heat sink comprises a plurality of fins, a portion of said plurality of fins are disposed within said air scoop and an opposite portion of said plurality of fins are disposed externally to said outlet end.

17. The air sanitizing apparatus arranged within said HVAC duct recited in claim 16, wherein said UV light module further comprises a plurality of UV LEDs secured to said PCB, each of said plurality of individual heat sinks is disposed adjacent to each of said plurality of UV LEDs.

18. The air sanitizing apparatus arranged within said HVAC duct recited in claim 14, wherein each of said plurality of individual heat sinks comprises a plurality of fins.

19. The air sanitizing apparatus arranged within said HVAC duct recited in claim 14, wherein when said ambient temperature sensor and said heat-source temperature sensor collect temperatures that are closer in degrees said microcontroller communicates to said UV light module to turn on, wherein when said ambient temperature sensor and said heat-source temperature sensor collect temperatures that are farther in degrees said microcontroller communicates to said UV light module to turn off.

20. The air sanitizing apparatus arranged within said HVAC duct recited in claim 14, wherein said control board is housed in a control module, said control module arranged on said HVAC duct, said control module in electrical communication with an external power source, said control module in electrical communication with said UV light module.

* * * * *